(12) United States Patent
Blondek et al.

(10) Patent No.: US 12,201,439 B2
(45) Date of Patent: Jan. 21, 2025

(54) SKIN ANALYSIS DEVICE

(71) Applicant: IIAA LIMITED, Borehamwood (GB)

(72) Inventors: Alex Blondek, Borehamwood (GB); Daniel Richard Walmsley, Borehamwood (GB); Gary David Ross, Borehamwood (GB); Jeremy Frank Saunders, Borehamwood (GB); Richard Kier Bebbington, Borehamwood (GB)

(73) Assignee: IIAA LIMITED, Borehamwood (GB)

( * ) Notice: Subject to any disclaimer, the term of this patent is extended or adjusted under 35 U.S.C. 154(b) by 944 days.

(21) Appl. No.: 17/280,383

(22) PCT Filed: Sep. 27, 2019

(86) PCT No.: PCT/GB2019/052736
§ 371 (c)(1),
(2) Date: Mar. 26, 2021

(87) PCT Pub. No.: WO2020/065340
PCT Pub. Date: Apr. 2, 2020

(65) Prior Publication Data
US 2021/0338147 A1 Nov. 4, 2021

(30) Foreign Application Priority Data

Sep. 27, 2018 (GB) ........................ 1815799

(51) Int. Cl.
*A61B 5/00* (2006.01)
*G03B 15/03* (2021.01)
(Continued)

(52) U.S. Cl.
CPC ............ *A61B 5/441* (2013.01); *A61B 5/0077* (2013.01); *G03B 15/03* (2013.01); *H04N 23/51* (2023.01);
(Continued)

(58) Field of Classification Search
CPC . A61B 5/441; A61B 5/0077; A61B 2562/185; H04N 23/51; H04N 23/74; H04N 23/56; G03B 15/03
See application file for complete search history.

(56) References Cited

U.S. PATENT DOCUMENTS

2004/0218810 A1* 11/2004 Momma .............. A61B 5/0064
382/162
2006/0092315 A1* 5/2006 Payonk ................. A61B 5/445
348/370
(Continued)

FOREIGN PATENT DOCUMENTS

FR 2987908 A1 9/2013
JP 2005211581 A * 8/2005 ........... A61B 5/0059
(Continued)

OTHER PUBLICATIONS

International Search Report for PCT/GB2019/052736 dated Jan. 2, 2020, 5 pages.

*Primary Examiner* — Chao Sheng
(74) *Attorney, Agent, or Firm* — Viksnins Harris Padys Malen LLP

(57) ABSTRACT

A device for photographing a human face comprising: a) a light-excluding housing configured to receive a human face at an aperture in said housing; and b) a stand on which the light-excluding housing is mounted at one or more (preferably two rotatable pivot points, such that rotation about said pivot points results in movement of the aperture upwards and/or downwards.

12 Claims, 17 Drawing Sheets

(51) Int. Cl.
*H04N 23/51* (2023.01)
*H04N 23/56* (2023.01)
*H04N 23/74* (2023.01)

(52) U.S. Cl.
CPC ............ *H04N 23/56* (2023.01); *H04N 23/74* (2023.01); *A61B 2562/185* (2013.01)

(56) References Cited

U.S. PATENT DOCUMENTS

| | | |
|---|---|---|
| 2009/0059028 A1 | 3/2009 | Kollias et al. |
| 2011/0098229 A1 | 4/2011 | Paul |
| 2015/0304530 A1 | 10/2015 | Courteille et al. |
| 2016/0247017 A1* | 8/2016 | Sareen ................ A61B 5/7475 |
| 2019/0117379 A1* | 4/2019 | Quirós ..................... A61F 2/12 |

FOREIGN PATENT DOCUMENTS

| | | | |
|---|---|---|---|
| JP | 2007158395 A | * | 6/2007 |
| JP | 2008161508 A | * | 7/2008 |
| JP | 2008289706 A | * | 12/2008 |
| JP | 2014-517059 A | | 7/2014 |
| WO | 2012175743 A2 | | 12/2012 |
| WO | 2014139934 A1 | | 9/2014 |
| WO | 2017161454 A1 | | 9/2017 |

* cited by examiner

SKIN ANALYSIS DEVICE

CROSS REFERENCE TO RELATED APPLICATION

This application is a 35 U.S.C. 371 National Phase Entry Application from PCT/GB2019/052736, filed Sep. 27, 2019, which claims priority to United Kingdom Patent Application No. 1815799.0, filed Sep. 27, 2018, the disclosures of which are incorporated herein in their entirety by reference, and priority is claimed to each of the foregoing.

INTRODUCTION

Background to the Invention

The analysis of complexion is a procedure which is carried out in order to assess the health of skin and the extent to which it is showing signs of ageing and/or other damage. Having this information can help predict an individual's future complexion and also be used to guide the selection of a cosmetic or medical treatment to prevent further skin damage and/or effect complexion improvements. Before and after analysis can be used to assess the efficacy of a skin treatment, both in an R & D context and in the context of an individual's complexion where the individual can be provided with evidence that a skin care regime which they are following is beneficial to them or not. This allows non-beneficial treatments to be stopped or replaced by more effective treatments and provides reassurance and motivation for the continuation of beneficial treatments.

Analysis can be carried out by computer software or by eye by a trained professional, but in all cases starts with capturing a photographic image of the complexion. Although applicable to the skin on any part of the body, the photographic image is usually taken of the subject's face.

A photograph taken in visible white light can be useful in identifying spots and wrinkles and also enlarged pores and raised textures, which influence skin smoothness. Sun damage can be detected as spots under UV illumination and illumination under red light can be used to highlight red areas of skin such as those caused by spider veins and inflammation.

Commercial skin analysis devices are available consisting of a chin rest on which the subject places their chin. The device then takes a photograph under various illumination conditions. The camera and the illuminating lamps can move together relative to the subject's face so that photographs may be taken looking directly at the face and at offset angles to either side.

The present invention provides an improved device which utilizes a light excluding housing to exclude ambient light thereby improving image quality. Devices of the present invention include those wherein the housing is mounted on a stand at one or more rotatable pivot points, such that rotation about such pivot points results in movement up or down of an aperture to receive a user's face, such that the device is able to accommodate conveniently users of differing heights without their necessarily noticing that the device has been adjusted to accommodate them. Devices of the present invention also include those in which a camera lens and a light source are cross polarized to each other and arranged in particularly advantageous ways. Devices of the present invention also include those in which the camera is moved relative to, and inside of, the housing so as to minimize the parts of the device subject to movement and results in a smaller, lighter and more compact device and also allows for greater consistency of image illumination and position which is important for comparison purposes. Such devices may provide illumination with polarized light from a light source which surrounds and is close to the camera lens so that the light source moves together with the camera lens. Further advantages relating to preferred embodiments of the device include features to reduce claustrophobia, and devices further comprising skin hydration probes. The present invention also includes devices incorporating combinations of two or more of the features referred to above.

SUMMARY OF THE INVENTION

The present invention in its first aspect provides a device for photographing a human face comprising:
  a) a light-excluding housing configured to receive a human face at an aperture in said housing; and
  b) a stand on which the light-excluding housing is mounted at one or more (preferably two) rotatable pivot points, such that rotation about said pivot points results in movement of the aperture upwards and/or downwards.

The present invention in its second aspect provides a method of providing images of a human face comprising, placing the face at an aperture of a light excluding housing and pivoting the light excluding housing upwards or downwards in order to adjust the height of the aperture so as to match it to the height at which the face is located.

The present invention provides in its third aspect a device for photographing a human face comprising:
  a) a light-excluding housing configured to receive a human face at an aperture in said housing; and
  b) a camera and a light source mounted inside the housing, wherein the mounting is configured so that the camera and light source are moveable together relative to the housing;
wherein the camera comprises a lens having an optical axis and the light source is configured to illuminate a human face to be received at the aperture, and wherein the camera lens is provided with a linear polarization filter and the light source is configured to produce illumination which is cross polarized relative to said linear polarization filter, wherein the angle between the light source and the camera lens is less than 30 degrees wherein the angle is measured at a point 200 mm along the optical axis from the camera lens.

The present invention in its forth aspect provides a method of providing images of a human face placed at an aperture of a light-excluding housing comprising illuminating the human face with linearly-polarized light, and capturing an image of the face with a camera having a lens with a linear polarization filter which is cross-polarized relative the illumination, wherein the angle between the light source and the camera lens is less than 30 degrees wherein the angle is measured at a point 200 mm along the optical axis from the camera lens

DETAILED DESCRIPTION OF THE INVENTION

Figure 1:
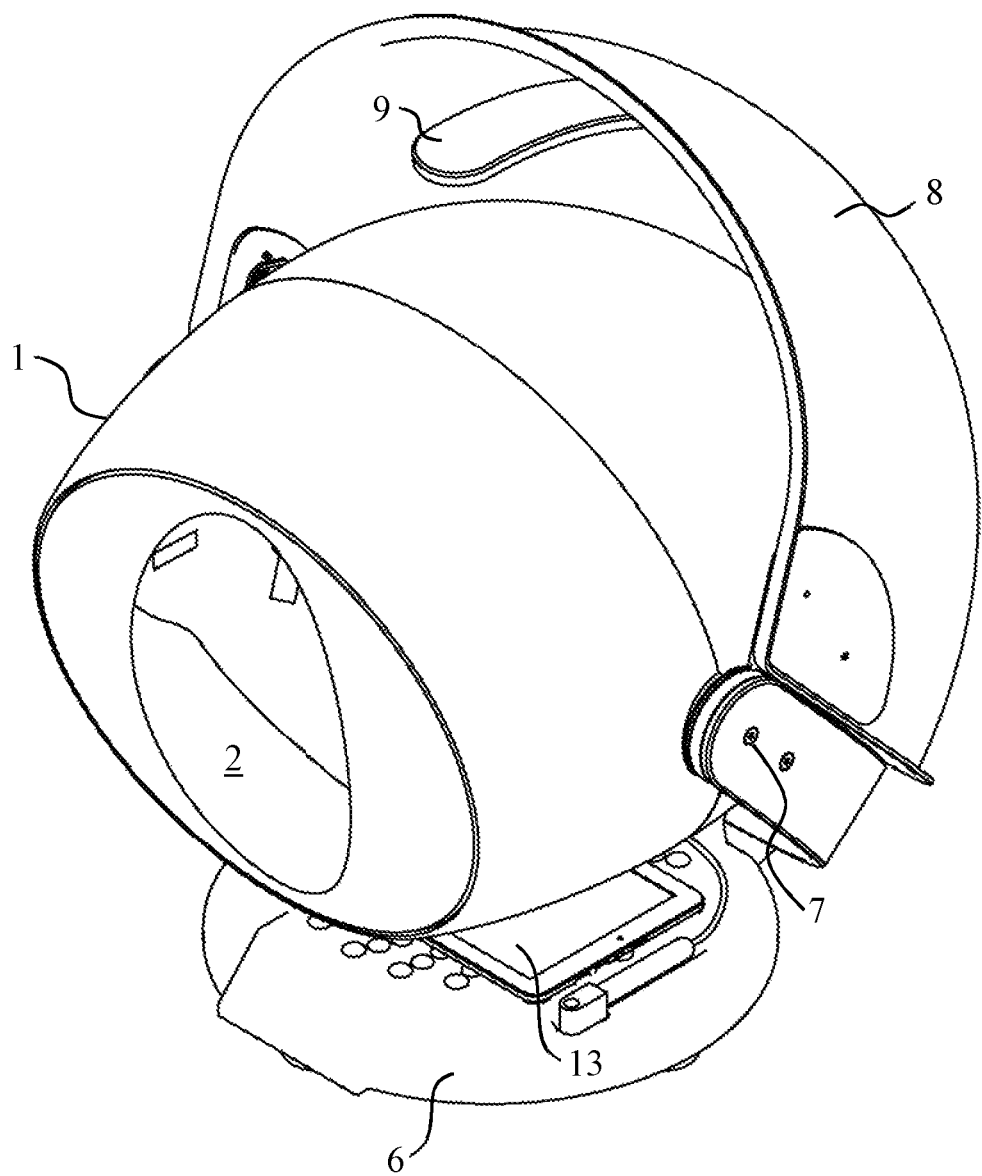
FIGS. 1 to 4 show an embodiment of a device according to the invention in a "shroud open" position.

First and Second Aspects of the Invention

The present invention in its first aspect provides a device for photographing a human face comprising:
a) a light-excluding housing configured to receive a human face at an aperture in said housing; and
b) a stand on which the light-excluding housing is mounted at one or more (preferably two) rotatable pivot points, such that rotation about said pivot points results in movement of the aperture upwards and/or downwards.

The present invention in its second aspect provides a method of providing images of a human face comprising, placing the face at an aperture of a light excluding housing and pivoting the light excluding housing upwards or downwards in order to adjust the height of the aperture so as to match it to the height at which the face is located.

Camera

According to the first and second aspects of the invention, the device preferably includes a camera which is preferably a digital camera of at least 1 mega pixel (for example at least 5 or 10 mega pixel resolution). The camera preferably is configured to provide its output to a device, for example a desktop, laptop or tablet computer external to the housing. Various camera settings can be adjusted either automatically or manually. For example automatic settings can be used to obtain a well-illuminated picture. According to some embodiments it is preferred that the camera settings are manually adjustable. This may assist in ensuring that the images captured are consistent with earlier-captured images which can make comparison between pictures easier.

Camera Mounting

According to the first and second aspects of the invention, the camera, when present in the device, is preferably mounted inside the housing. Preferably it is mounted on the inside wall of the housing substantially opposite the aperture. The mounting preferably allows the camera to move. Preferably, this movement is in a substantially horizontal direction between a position directly opposite the aperture to positions horizontally ±10, 20 or 30 degrees lateral to the position directly opposite the aperture. The mounting is preferably configured so that the movement is about an arc, such that the distance between the camera and a face received at the aperture remains substantially constant as the camera moves thus allowing for images of substantially equal size to be captured without the use of a zoom lens and also allowing for the optional use of a fixed focus lens, thus potentially simplifying the camera required and producing images with a greater degree of standardization. The mounting preferably comprises one or two rails on which a carriage carrying the camera moves. The rails may consist of an upper rail and a lower rail, wherein the upper rail is substantially above the lower rail. The mounting preferably comprises an electric drive means by which the carriage is moved along the rail. Any suitable drive means may be used, for example a lead screw or a pulley and belt system. The movement of the carriage and, therefore, the position of the camera is preferably controlled by a computer, for example a desktop, laptop or tablet computer, which may be external to the housing. Preferably, the camera is mounted so as to be between 50 and 500 mm, for example between 80 and 400 mm, for example between 100 and 300 mm, for example between 120 and 280 mm, for example between 150 and 250 mm, for example between 170 and 230 mm form a face received in the aperture.

Illumination

According to the first and second aspects of the invention, the housing preferably includes means to illuminate a human face received at the aperture. This illumination means may comprise any suitable electrically driven light source, for example incandescent lights, fluorescent tubes, flash tubes or LEDs. Preferably, the light source comprises LEDs (for example banks of arrayed LEDs), because of their high efficiency and low heat output.

The illumination is preferably provided at multiple locations within the housing (for example as multiple banks of arrayed LEDs). According to certain embodiments, the locations are symmetrically arranged within the housing and include locations directly opposite the aperture and locations to either side. According to other preferred embodiments the illumination is mounted so that it moves together with the camera. For example a bank of LEDs may be provided either side of the camera. According to certain preferred embodiments, the illumination is provided by illumination means such as LEDs arrayed in a continuous or discontinuous ring around the lens of the camera and mounted so as to move together with the camera. A similar arrangement may be adopted even when the camera is not configured to move inside the housing.

The illumination means preferably provides light which is cross polarized relative to a polarization filter provided on the lens of the camera. Preferred features of polarization and illumination arrangements are optionally as described with reference to aspects 3 and 4 of the invention. The illumination is preferably controlled by a computer, for example a laptop, desktop or tablet computer external to the housing. Preferably, this control is integrated with the control of image capture and camera position. Preferably, the illumination is controlled such that its brightness is adjusted in dependence of the position of the camera. This is optionally configured to reduce illumination from the same direction as the camera is positioned in order to reduce reflections in the image from direct illumination.

According to certain embodiments of the first and second aspects of the invention, the illumination is provided by multiple banks of arrayed LEDs and within each array of LEDs there is provided LEDs providing different illumination. For example, the arrays may comprise LEDs providing both un-polarized and polarized light. This allows convenient switching between polarized illumination and un-polarized illumination by switching the relevant LEDs within the array on or off. This is a mechanically simpler arrangement than moving filters in front of the illumination means (or alternatively the camera). Preferably, arrays of LEDs in accordance with the invention include at least some LEDs providing polarized illumination and some LEDs providing un-polarized illumination. Additionally or alternatively, the arrays of LEDs in accordance with the invention include at least some LEDs providing illumination at a first wavelength and at least some LEDs providing illumination at a second wavelength, for example illumination at a visible wavelength such as 400 to 700 nm, and illumination at a UV wavelength such as 365 nm.

For certain applications, it will be necessary to illuminate the face with bright light in order to capture a high quality photographic image in a sufficiently short time. Whilst such bright light would not be regarded as dangerous, it may be uncomfortable ("dazzling"). In order to mitigate this, the illumination means are preferable configured to illuminate the face at full intensity only during image capture and preferably for no longer than 1 second (of example less than 0.5 or 0.3 seconds). Outside of those times the illumination means may be switched off or may be configured to illuminate the face at a lower intensity in the interests of user comfort, energy efficiency and in order to prolong the service life of the illumination means.

According to certain preferred embodiments of the first and second aspects of the invention, the illumination may have one or more of the features of the third and fourth aspect of the invention, for example the direction of illumination and the polarization of the light produced may be as described in reference to the third and fourth aspects.

Mounting of Housing

According to the first and second aspects of the invention, the housing is mounted on a stand at one or more (for example one or two, preferably two) rotatable pivot points which are preferably co-axial to each other, such that rotation about said pivot points results in movement of the aperture upwards and/or downwards.

This pivoting arrangement is advantageous because it allows the device to be used by a subject of various heights without requiring the device to be adjusted other than by pivoting of the housing. When the device is placed at table-top height and the subject is seated in an ordinary chair, a subject who is relatively short in stature will naturally look upwards into a housing which has a downward tilting aperture and a subject who is relatively tall in stature will naturally look downwards into a housing which has an upward tilting aperture. If the housing is approximately neutrally balanced and the pivot points arranged so as to allow free movement, this adjustment to different heights will happen easily and unconsciously as will any backward or forward movement of the subject's chair required to accommodate the position of the face. Thus subjects of a wide range of statures are able to be accommodated in the device with maximum comfort and convenience and minimum "fuss". Such an arrangement may also minimize facial distortion caused by a poorly adjusted device resulting in an image which is superior and more consistent with other images captured with the same (or similar) devices at different times. Exceptionally if a subject of unusually short or unusually tall stature wishes to use the device and is outside of the range of statures that may be accommodated by means of tilting the housing, they may be accommodated by moving the device to a lower or higher table or making use of a lower or higher chair as appropriate. It is preferred for the pivot points to be provided with sufficient resistance so that housing when pivoted up or down into whatever position required stays in that position without needing to be held, but that the resistance is low enough to permit easy movement between different positions. In preferred embodiments, the device is approximately balanced about the pivot points to also assist in both easy of pivoting and maintenance of position. The pivot points may comprise a clutch mechanism or rotary damper to allow the shroud to hold itself in any position, for example in an open position. Preferably such a clutch mechanism or rotary damper is arranged to provide a soft closure mechanism so that the shroud may be moved between an open and a closed position but that it does not need to be held open whilst the face is placed at the aperture and so that when the face is in place it can be pulled down behind the head and does not drop down in an uncontrolled manner onto the shoulders.

A method according to the second aspect of the invention preferably includes the sequence of:
 a) Placing a face at an aperture of a light excluding housing wherein the housing tilts to cause the aperture to move up and down in order to adjust its height to the height of the face;
 b) Optionally, placing a light excluding shroud (having one or more of the features described above in reference to the first aspect of the invention) behind the head of the person who has their face at the aperture.
 c) Optionally, moving a camera within the housing between a position suitable for taking an image of the front of the face and a position suitable for taking an image of the side of the face, wherein at each position any windows in the housing are occluded and the face is illuminated by light produced by illumination means interior to the housing
 d) Taking one or more image of the face using the camera.
 e) Optionally transferring the images to a computer, for example a tablet computer external to the housing.

The illumination means, the windows, the shroud, and the housing, and the illumination means, and positioning and control thereof, camera, camera position and transparency of the windows may optionally be as described above in reference to the first and/or third aspects of the invention.

The method of the invention may optionally include steps subsequent to steps a) to e). Those optional steps may include automatic image analysis by appropriate image analysis software. They may include the presentation of images for analysis by a trained human analysist. They may include presentation of side by side images for analysis so that changes in complexion as a result of the passage of time or the use of a specific treatment of the skin or body may be assessed.

The method may optionally include subsequent steps of selecting a suitable skin care product or cosmetic treatment and recommending it or providing it to the subject. Methods of the invention may include subsequent steps of giving advice on lifestyle factors such as diet or sun exposure so as to improve skin condition or reduce skin ageing or damage.

Methods of the invention may be used to categorize a subject as having a particular skin-type so that they are able to select cosmetic products best suited to their skin type.

Methods of the invention may be used to assist the monitoring of a treatment. For example in a patient undergoing a hair removal or tanning treatment, a method of the invention may be used to assess the extent of skin damage caused by that treatment in order that it be kept below a threshold of unacceptable damage Methods of the invention may be used for the monitoring a skin treatment in order to study the effect of a particular compound or composition on the skin of an experimental volunteer.

Third and Fourth Aspects of the Invention

Use of Polarized Light

The present invention provides in its third aspect a device for photographing a human face comprising:

a) a light-excluding housing configured to receive a human face at an aperture in said housing; and
b) a camera and a light source mounted inside the housing, wherein the mounting is configured so that the camera and light source are moveable together relative to the housing;

wherein the camera comprises a lens having an optical axis and the light source is configured to illuminate a human face to be received at the aperture, and wherein the camera lens is provided with a linear polarization filter and the light source is configured to produce illumination which is cross polarized relative to said linear polarization filter, wherein the angle between the light source and the camera lens is less than 30 degrees wherein the angle is measured at a point 200 mm along the optical axis from the camera lens The present invention in its fourth aspect provides a method of providing images of a human face placed at an aperture of a light-excluding housing comprising illuminating the human face with linearly-polarized light, and capturing an image of the face with a camera having a lens with a linear polarization filter which is cross-polarized relative to the illumination, wherein the angle between the light source and the camera lens is less than 30 degrees wherein the angle is measured at a point 200 mm along the optical axis from the camera lens Preferably the angle is less than 28, 26, 25, 24, 23, 22, 21, 20, 19, 18, 17, 16, 15, 14, 13, 12, 11, 10, 9, 8, 7, 6, 5, 4 or 3 degrees. The advantage provided by this arrangement is that it produces "straight on" illumination of the face with polarized light which has been found to produce better images than if the polarized light is provided at a position which is not essentially "straight on" with respect to the optical axis of the camera. This is because polarized light provided at wider angles to the optical axis of the camera lens reflect off the inside of the housing and/or face and so loose some of the coherency of its polarization.

The use of cross polarized illumination reveals redness beneath the skin which would otherwise not be visible from the surface, but may be indicative of skin damage or ageing.

Camera

According to the third and fourth aspects of the invention, the device includes a camera which is preferably a digital camera of at least 1 mega pixel (for example at least 5 or 10 mega pixel resolution). The camera preferably is configured to provide its output to a device, for example a desktop, laptop or tablet computer external to the housing. Various camera settings can be adjusted either automatically or manually. For example automatic settings can be used to obtain a well-illuminated picture. According to some embodiments it is preferred that the camera settings are manually adjustable. This may assist in ensuring that the images captured are consistent with earlier-captured images which can make comparison between pictures easier. According to the third and fourth aspects of the invention, the camera comprises a camera lens which is provided with a linear polarization filter.

Camera Mounting

According to the third and fourth aspects of the invention, the camera is mounted inside the housing. Preferably it is mounted on the inside wall of the housing substantially opposite the aperture. The mounting preferably allows the camera to move. Preferably, this movement is in a substantially horizontal direction between a position directly opposite the aperture to positions horizontally ±10, 20 or 30 degrees lateral to the position directly opposite the aperture. The mounting is preferably configured so that the movement is about an arc, such that the distance between the camera and a face received at the aperture remains substantially constant as the camera moves thus allowing for images of substantially equal size to be captured without the use of a zoom lens and also allowing for the optional use of a fixed focus lens, thus potentially simplifying the camera required and producing images with a greater degree of standardization. The mounting preferably comprises one or two rails on which a carriage carrying the camera moves. The rails may consist of an upper rail and a lower rail, wherein the upper rail is substantially above the lower rail. The mounting preferably comprises an electric drive means by which the carriage is moved along the rail. Any suitable drive means may be used, for example a lead screw or a pulley and belt system. The movement of the carriage and, therefore, the position of the camera is preferably controlled by a computer, for example a desktop, laptop or tablet computer, which may be external to the housing.

Illumination

According to the third and fourth aspects of the invention, the housing includes a light source mounted inside the housing and arranged to illuminate a human face received at the aperture. Light source is configured to produce illumination which is cross-polarized (ie polarized at right angles) relative to the linear polarization filter on the camera lens. The light source may be chosen to produce polarized light either as an intrinsic property or by means of a polarization filter as part of the light source. The light source may comprise any suitable electrically driven light source, for example incandescent lights, fluorescent tubes, flash tubes or LEDs. Preferably, the light source comprises LEDs (for example banks of arrayed LEDs), because of their high efficiency and low heat output.

According to devices of the third aspect of the invention, the light source is configured to produce illumination from a direction which is substantially aligned with the optical axis of the camera lens. This means that if the illumination means comprises a polarizing filter that filter will be in substantially the same plane as the polarization filter on the camera.

According to embodiments wherein the camera moves inside the housing, the illumination is preferably mounted so as to move together with the camera. For example it may be provided as continuous or discontinuous ring of LEDs arranged around the camera lens. A similar arrangement may be adopted even when the camera is not arranged to move inside the housing.

The light source is preferably controlled by a computer, for example a laptop, desktop or tablet computer external to the housing. Preferably, this control is integrated with the control of image capture and camera position.

Devices of the third aspect of the invention may optionally have in addition to the polarized light source detailed above, additional illumination means providing alternative illumination, for example illumination with unpolarized light. Such a device would be configured to allow convenient switching between polarized illumination and un-polarized illumination. This is a mechanically simpler arrangement than removing polarization filters (or alternatively the camera).

For certain applications, it will be necessary to illuminate the face with bright light in order to capture a high quality photographic image in a sufficiently short time. Whilst such bright light would not be regarded as dangerous, it may be uncomfortable ("dazzling"). In order to mitigate this, the device is preferable configured to illuminate the face at full intensity only during image capture and preferably for no longer than 1 second (of example less than 0.5 or 0.3 seconds). Outside of those times the light may be switched off or may be configured to illuminate the face at a lower intensity in the interests of user comfort, energy efficiency and in order to prolong the service life of the light source.

According to certain preferred embodiments of the third and fourth aspects of the invention, the illumination may have one or more of the features of the first and second aspect of the invention. For example, the wavelengths of illumination and the control of the illumination may be as described by reference to those aspects.

Mounting of Housing

According to the Third and fourth aspects of the invention, the housing is preferably mounted on a stand at one or more (for example one or two, preferably two) rotatable pivot points, such that rotation about said pivot points results in movement of the aperture upwards and/or downwards as described by reference to the first and second aspects of the invention.

Preferred embodiments of the fourth aspect of the invention may include features presented as optional or preferred in respect of the first, second or third aspects of the invention. In particular a method of the invention may include use of a light excluding housing having one or more of the features or configuration of a housing as described herein. Preferably, the housing is part of a device as described above in reference to the first and/or third aspect of the invention.

All Aspects of the Invention

Light Excluding Housing

According to all aspects of the invention, the light excluding housing is such that, in use, it excludes at least 50, 60 or 70% of ambient light (i.e. room lighting of daylight from a source outside of the housing). Because the housing comprises an aperture to receive a human face, and the reception of the face at the aperture reduces ambient light leaking into the housing by wholly or partially blocking the aperture, measurements of light exclusion are preferably carried out with a face at the aperture. If the housing contains optional light-admitting windows as described below, measurements of light exclusion are carried out with the windows occluded to the transmission of light.

The housing may conveniently be made of any suitable material, for example it may be conveniently moulded or machined from a polymer resin. According to some embodiments, the interior surface of the housing is a non-reflective dark colour, for example black, preferably matt black. The outside of the housing may be any colour. The housing is preferably of a substantially spherical shape. The housing is preferably provided with one or both of a chin rest and a forehead rest, configured to hold the chin or forehead of a face received in the aperture.

The Aperture

According to all aspects of the invention, the aperture is configured to receive a human face. This means that it is preferably sized and shaped so that a human face (for example an adult human face) is substantially receivable at the aperture and substantially visible to a camera positioned inside the housing. The aperture is preferably substantially oval shaped and preferably not so large that an adult human is able to place their whole head inside the housing. The distance between the chin rest and forehead rest of a device having a substantially oval aperture and being provided with a chin and forehead rest may optionally be between 20 and 28 cm in its longer, vertical axis and between 12 and 18 cm in its shorter, horizontal axis Windows According to all aspects of the invention, the housing preferably includes one or more transparent or open windows through which a subject, having their face received at the aperture, is able to see forward to outside of the housing.

It is understood that, throughout this specification, reference to light-exclusion of the housing does not take into account the transparency or openness of the windows and that any such measurements or evaluation of the light exclusion of the housing are taken when the windows are made light excluding, closed or covered.

These windows advantageously provide a reduction in anxiety and/or claustrophobia when a face is received in the aperture and may also assist in encouraging the face to be placed correctly and the subject to look forward. When combined with a device having the pivoting arrangement of the first aspect of the invention, the ability of the user to look forward through the windows may subconsciously encourage them place their face correctly at the aperture and thereby allow the device to naturally adjust to their stature without them realizing that such an adaption has taken place.

It has been found to be advantageous if one or more windows (for example two windows) are provided in the housing, generally in the area of camera. This encourages the user to look forward though the windows and therefore generally towards the camera.

The window(s) may be provided with a means to close or cover them or to make them non-transmissible to light. For example, the windows may be provided with shutters or covers which are preferably electrically driven or controlled, for example by a computer used for controlling image capture and illumination. The windows are preferably glazed with switchable glass which may include electrochromic, photochromic or microblind technology. Preferably, the windows are able to switch between being transparent to being light excluding in less than 1 second. Preferably, the windows comprise electrochromic material and the device is configured so that the windows are normally transparent when the device is in use, except for short time periods (preferably less than 1 second), during which each image is captured.

Light Excluding Shroud

According to all aspects, devices of the invention optionally further comprise a light-excluding shroud. This shroud preferably is moveable to a position behind the head of a human subject who has placed his or her face so as to be received at the aperture. The shroud may be made of any suitable material, for example it may be a rigid or it may be a flexible textile material and it acts to reduce the ingress of ambient light in into the housing by reducing the amount of ambient light which reaches any gaps between the aperture and the face.

Preferably, the shroud is a rigid member which is moveable downwards behind the head of a subject after the subject has placed their head so that their face is received at the aperture of the device. Preferably this downward movement is achieved by rotation of the shroud about the pivot point or points of a device wherein the housing is mounted on a stand at one or more rotatable pivot points. That is to say, the device housing and the shroud are both mounted and rotatable about the same pivot point or pivot points. For example the device housing and the shroud may be co-axially mounted on a stand and rotatable about the one or more pivot points.

Preferably the shroud can also be moved downwards over the aperture when the device is not in use (i.e., when there is no face at the aperture). This may assist in protecting the parts of the device mounted inside the hood (especially the camera) from accidental damage and, to an extent, from dust.

Skin Analysis Probes

There are available a number of analysis probes which measure particular properties of skin. For example, skin moisture (hydration), sebum content, pH, transepidermal water loss (TEWL), and mechanical properties (including friction resistance and elasticity) may be measured using suitable probes. Courage and Khazaka electronics GmbH, Koln, Germany, produce a range of such probes.

According to all aspects of the present invention, devices may incorporate a hand-held probe to measure a one of the parameters referred to above. In particular devices may incorporate a hand-held probe for measuring skin hydration or TEWL. Such a probe may be incorporated as part of the device and be available for optional use alongside the rest of the device in methods of the invention. By being incorporated into a device of the invention, several advantages accrue. The probe can use the same power supply as the rest of the device and be sold as a single unit. Furthermore data obtained from the probe can be stored together with, or automatically cross-referenced with any images obtained. By having the image and the data from the probe available together, greater overall information about the state of the user's skin is obtained. Optionally, analysis of a photograph of a user can be used to decide (either automatically via a software algorithm or by exercise of judgement of a person viewing the photograph) whether the measurement via the probe should be obtained. For example if the photograph reveals skin damage characteristic of dry skin, a measurement of skin hydration or water loss may be conveniently obtained. According to some optional embodiments, the photograph may be used to assist in the selection of portions of skin to be probed. For example, a photograph may reveal localized skin damage which could suggest benefits in using a skin probe to obtain data from damaged (or undamaged) locations.

Further Features

The device according to all aspects of the invention, may optionally comprise a computer, for example a laptop or tablet computer which is configured to control image capture, control of lighting and movement of the camera. A conventional computer may be used (for example a Windows™ laptop or an Apple™ iPad™ or similar touch-screen tablet) and control of camera image capture, control of the motor controlling the position of the camera and control of the illumination means may be provided via a conventional input/output means (for example using a USB interface). The computer may be provided with suitable software for controlling the device and for ancillary tasks such as image storage. It may interface with a computer network (for example a wireless computer network) to enable it to interface with customer records and to transmit the captured images and other information to and from external storage, printers etc. so that the image can be shared with relevant persons and retained and used as required. According to some embodiments the captured images are stored on a remote server or in the cloud. This is advantageous because it permits easy access to the images from multiple locations. For example, a user can access their images from home and they can also be reviewed during a skin care consultation and any number of clinics (for example at any clinic with equipped with a device of the invention. In other embodiments they may be stored on a local server or on the computer (for example tablet computer) used to control the image capture, movement or camera and control of lighting.

The computer preferably comprises a display means ("screen") for displaying the images captured so that their quality can be assessed and so the subject can be shown the images obtained from their own face. Optionally, the computer may be programmed to show multiple images either sequentially or side-by-side so that it can be used to show how the condition of the complexion has changed over time or in response to treatment.

The computer may optionally comprise automatic image analysis. However, the inventors have found that for many uses it is preferred to simply display a high quality image to the human eye and allow a user to assess the condition of the subject's complexion using their experience and professional judgement.

The device may optionally be provided with a handle. This allows the device to be conveniently picked up and moved and minimizes the risk of accidental damage when this is done. Preferably, the device is provided with a stand on which the housing is mounted and the handle is attached to the stand but extends upwards to a position above the housing.

Because the device of the invention is preferably electrically powered it preferably includes a power supply for providing an appropriate electrical supply to the camera, means for moving the camera, illumination means and control computer. It may be convenient to provide that power supply in the stand part of the device.

A device according to the invention may be used in a method which comprises moving a camera within the housing between a position suitable for taking an image of the front of the face and a position suitable for taking an image of the side of the face, and capturing an image at each position.

Optionally, multiple images may be captured at each position. For example, images under different illumination conditions may be captured at each position.

A method of the invention according to the fourth aspect may include tilting the housing about an axis running through the interior of the housing such that the aperture moves up or down to a height suitable for the human face to be placed at the aperture with comfort and accommodating for differences in height between the face and the housing. The tilt may involve use of a device having one or more pivot points as described above.

Preferred embodiments of the second aspect of the invention may include features presented as optional or preferred in respect of the first, third or fourth aspects of the invention. In particular a method of the invention according to the second aspect may include methods of illuminating the skin with polarized light as described above by reference to the fourth aspect

EXAMPLES

An exemplary embodiment of the invention is described below in a non-limiting example and with reference to the drawings.

Device

FIG. 1 shows a general view of an embodiment of a device of the invention. Whilst such a device falls within the scope of a device according to both the first and third aspect of the invention, features of the first aspect are especially well shown in FIG. 1. As can be seen, the device comprises a light excluding housing (1), which has an aperture (2) which is dimensioned to receive a human face. The housing is mounted on a base (6), which may be conveniently placed on a table or counter. The whole device is reasonably portable and features a prominent carrying handle (9), by which it may be lifted and carried without damage. The device may comprise a computer, tablet or similar for controlling the device and/or displaying the images and this is shown in FIG. 1. The device also includes a hand-held probe (20) for measuring a property of the skin such as TEWL and this is also shown in FIG. 1.

Figure 2:
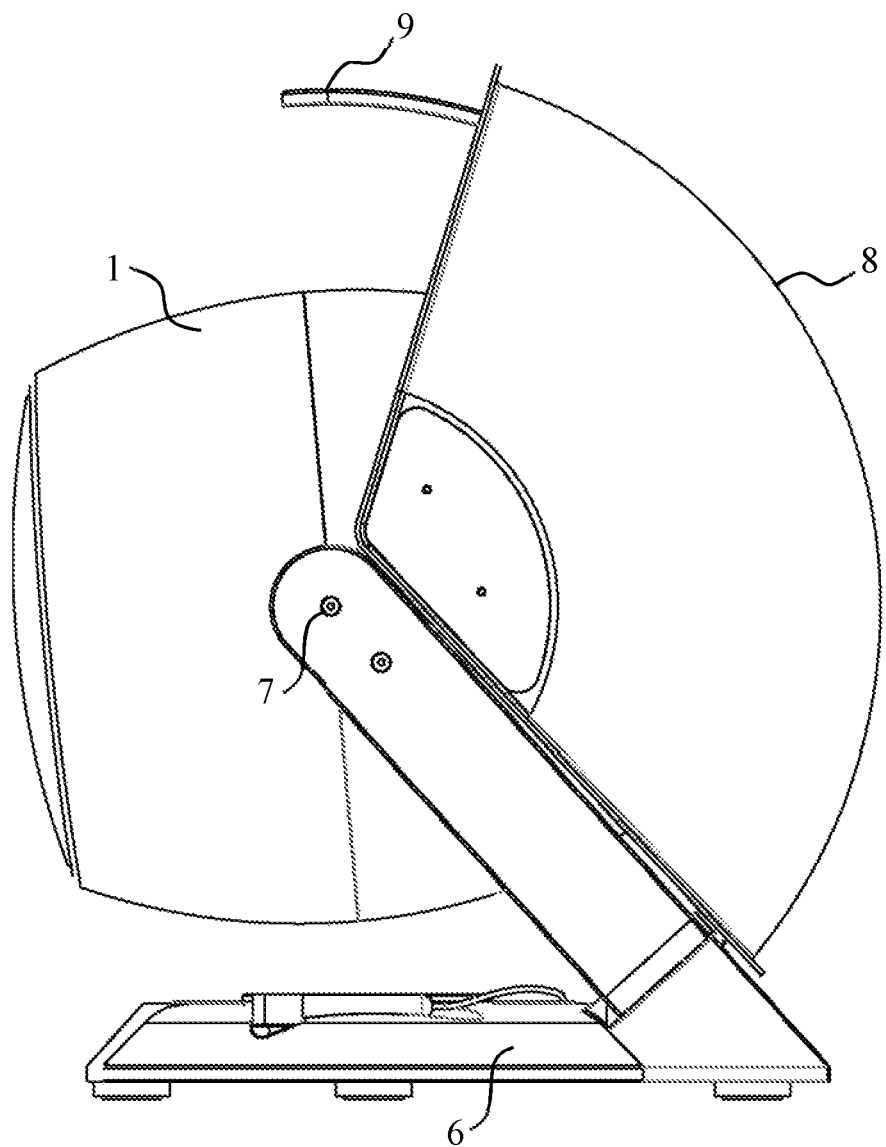
Figure 3:
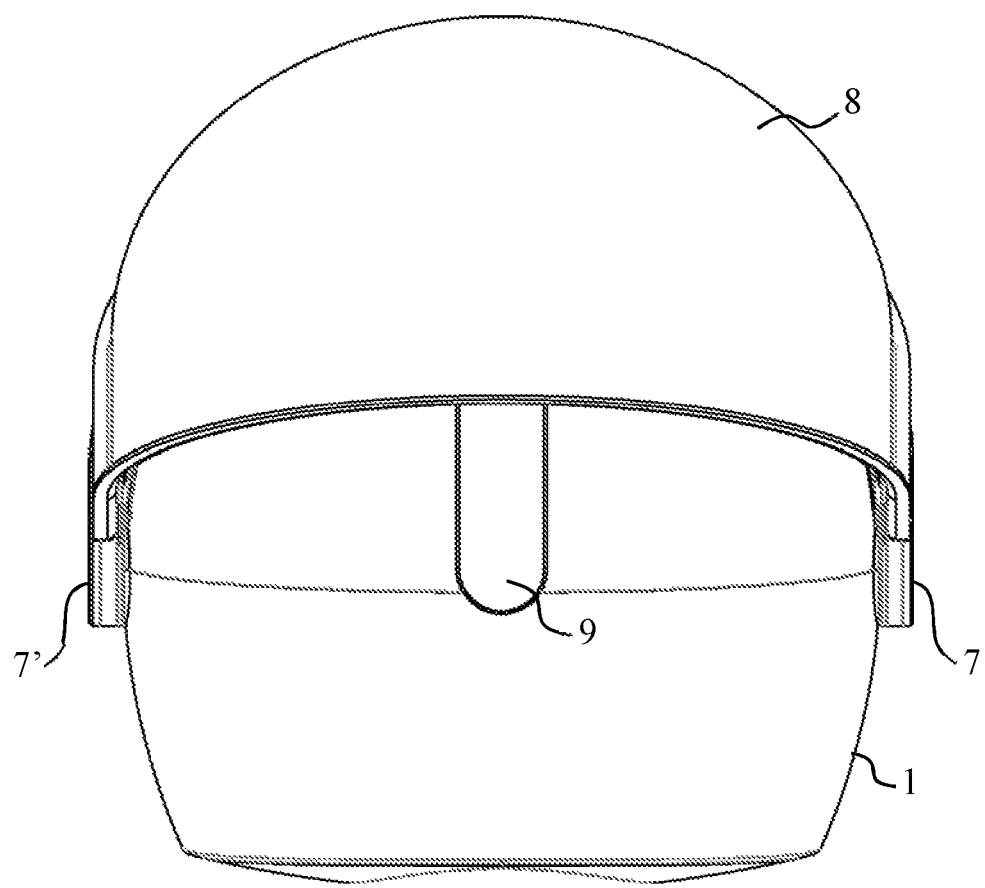

FIG. 2 shows the device of FIG. 1 from the side and clearly shows the position of the shroud (8) in the open position, wherein the handle (9) is exposed and accessible, as can also be seen in FIG. 3 which is a top view of the device of FIG. 1.

Figure 4:
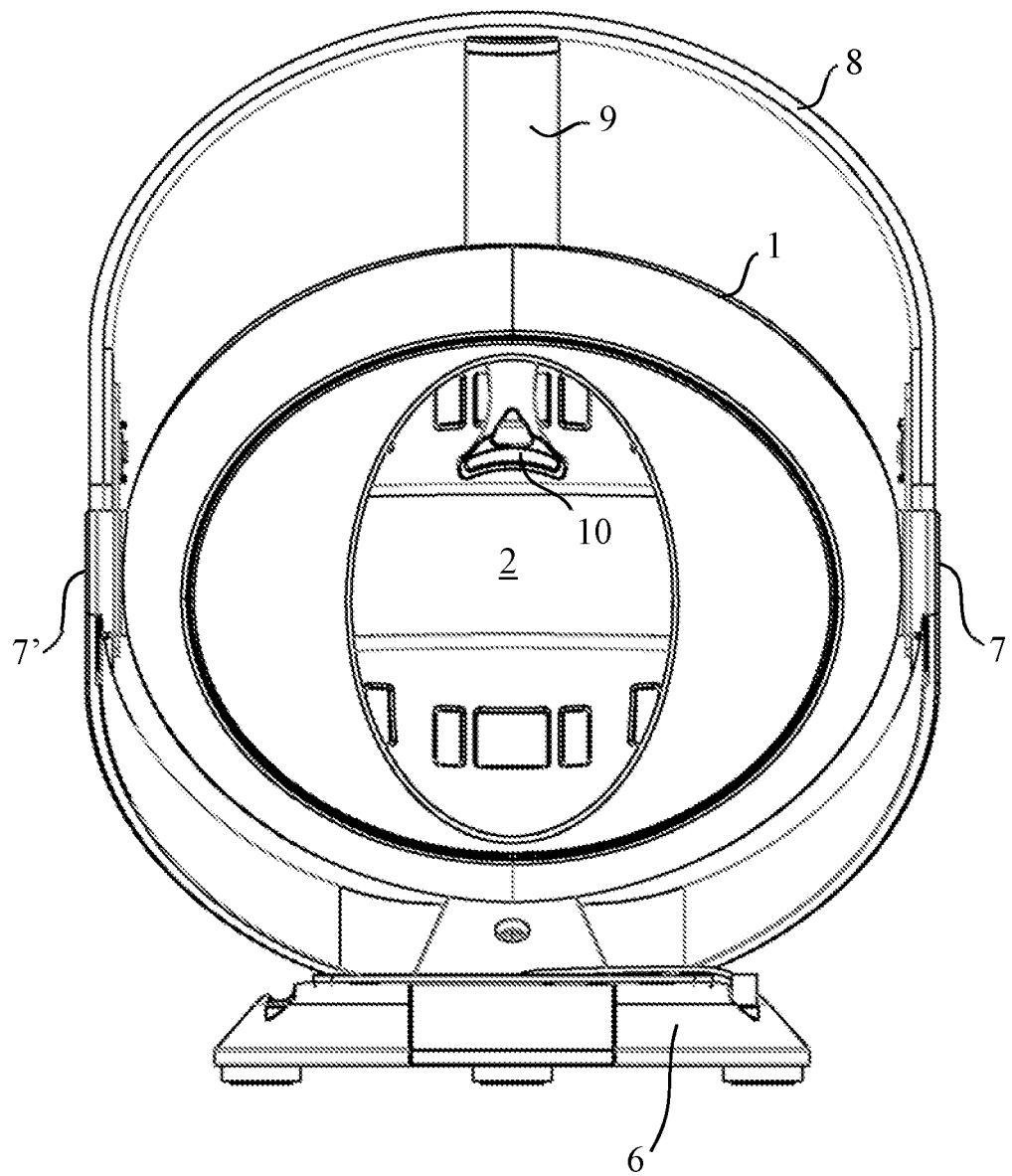
Figure 5:
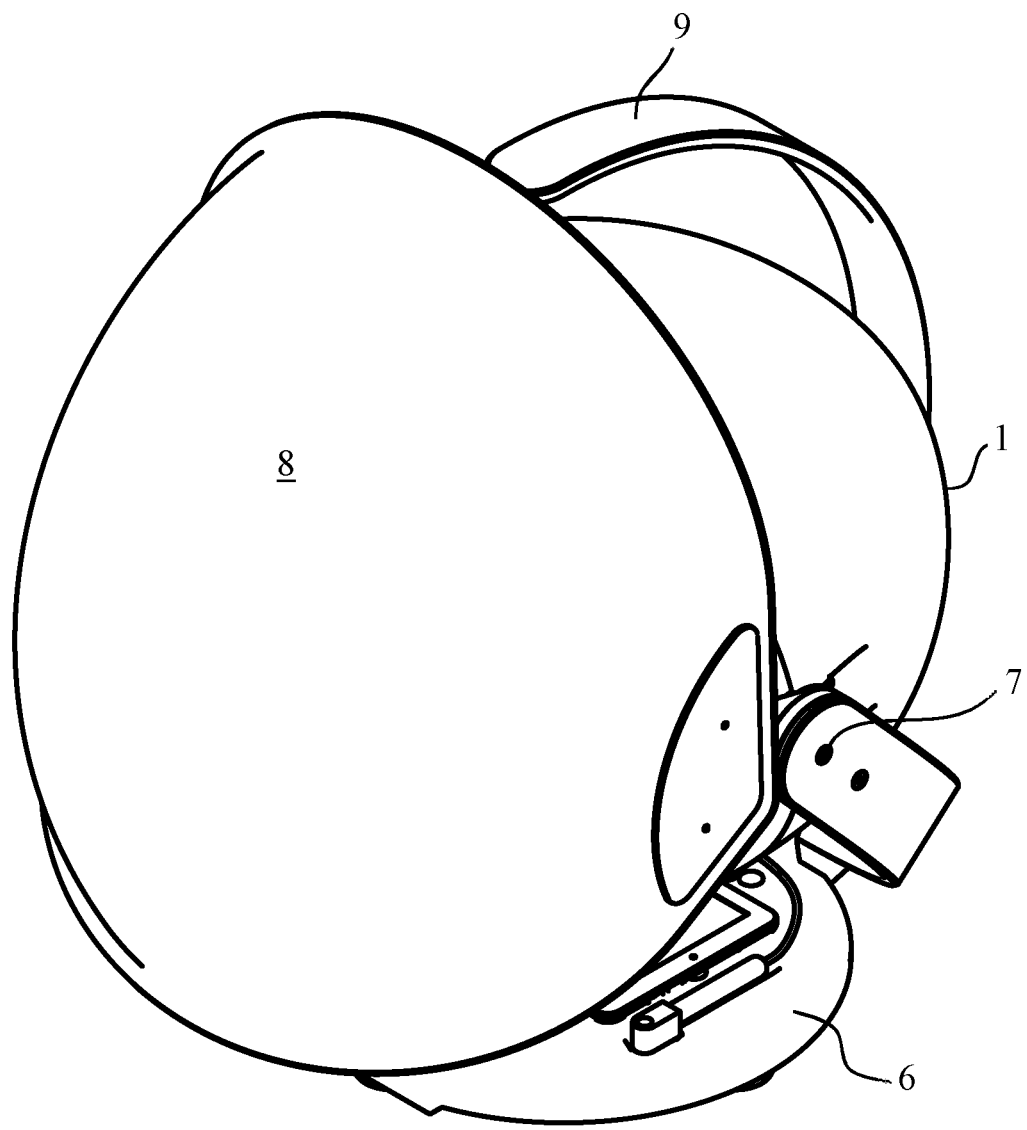
FIGS. 5 to 8 show an embodiment of a device according to the invention in a "shroud closed" position.
Figure 6:
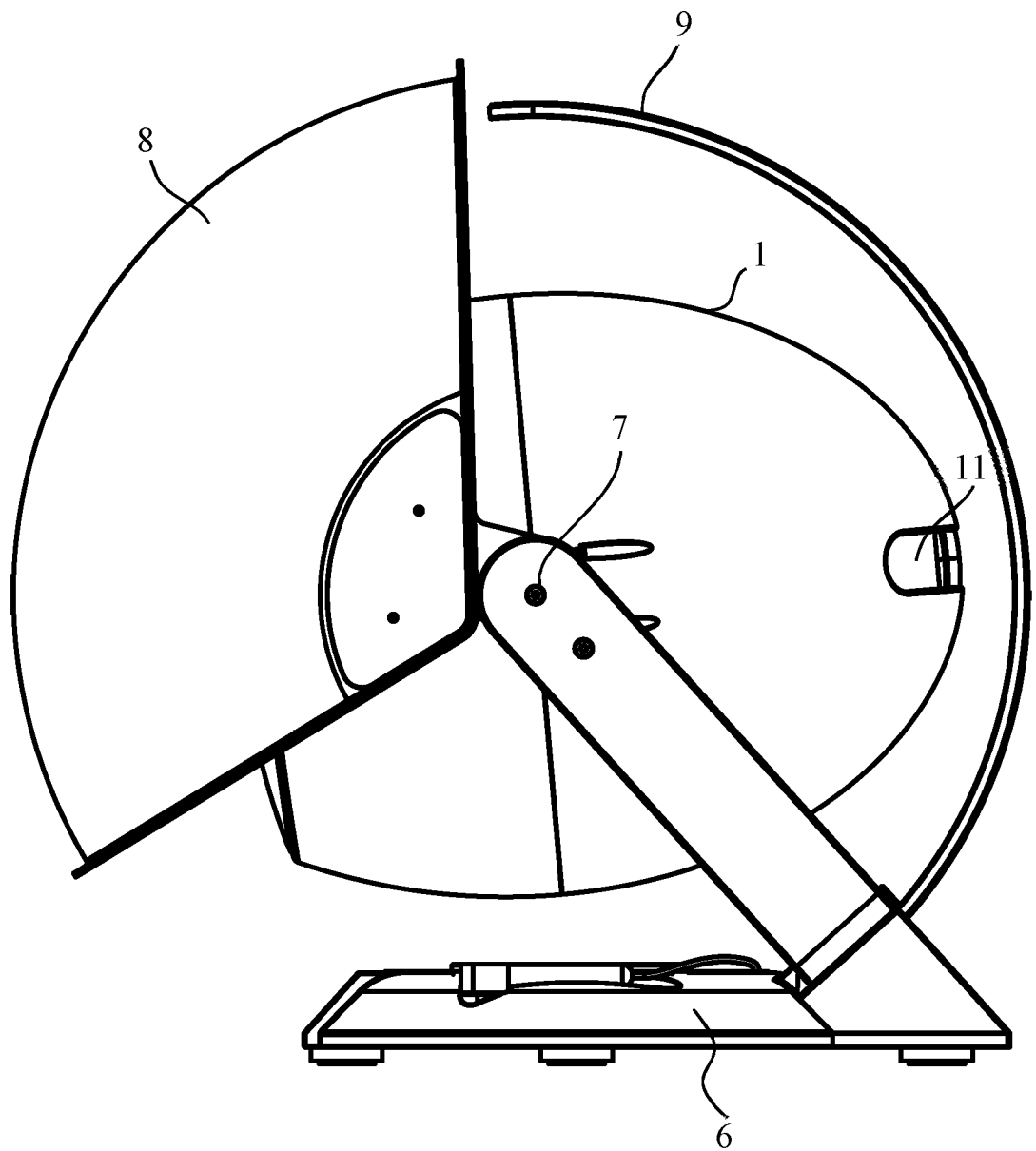
Figure 7:
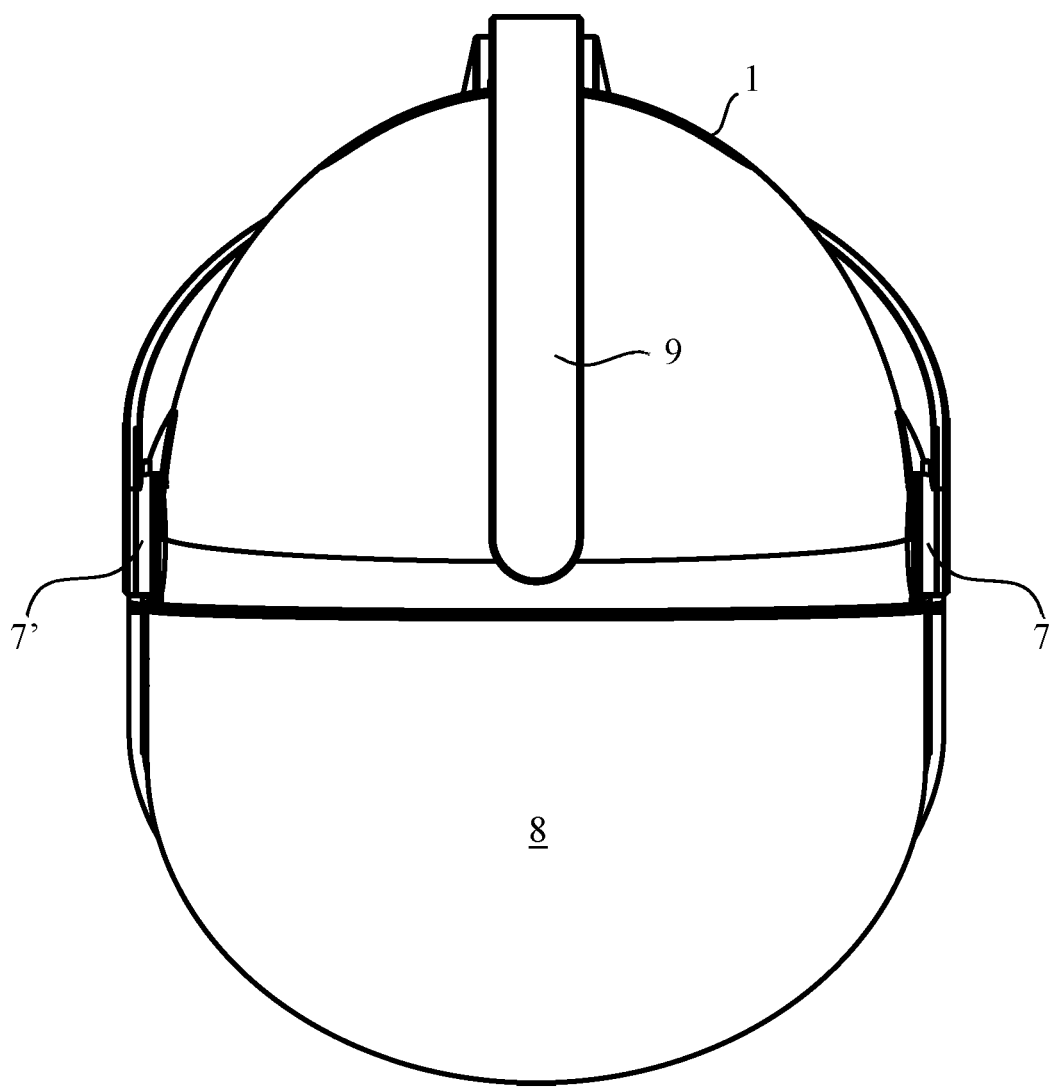
Figure 8:
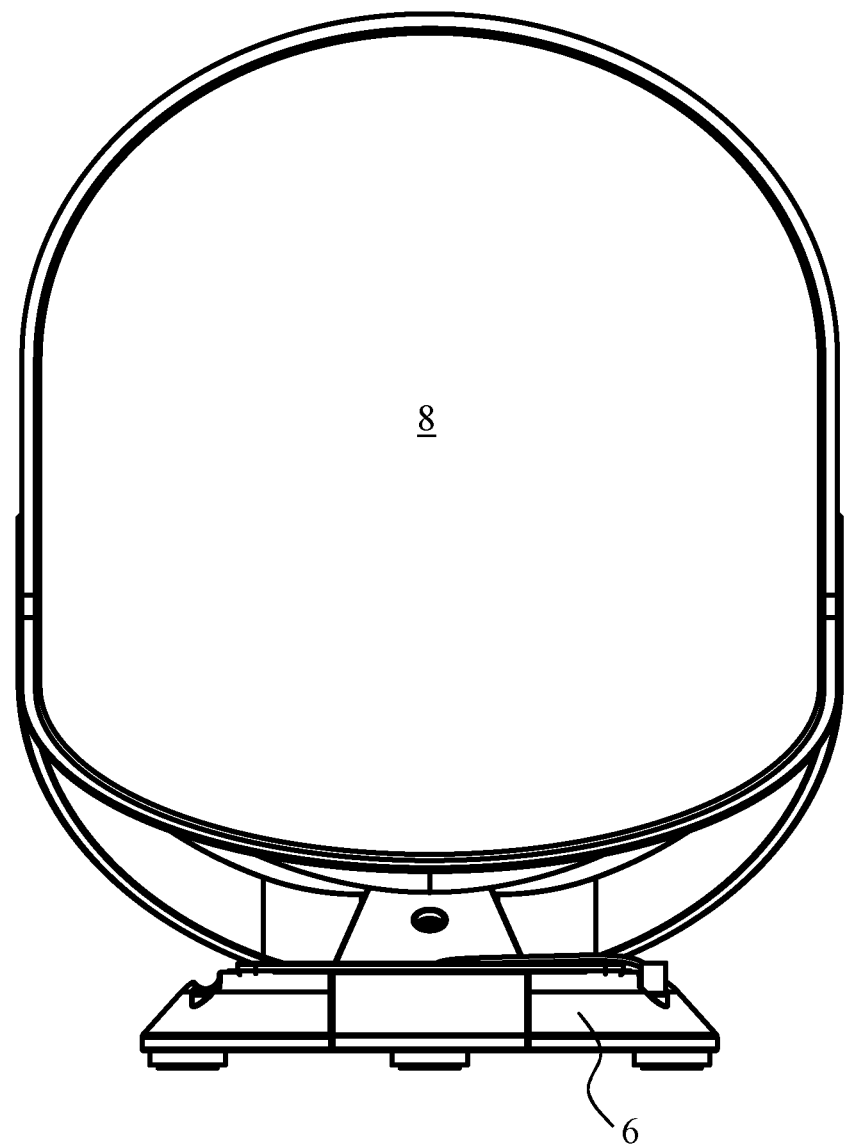

FIG. 4 shows a forehead rest (10) in the aperture to assist in positioning a face at the aperture.

FIGS. 5 to 8 correspond, respectively, to FIGS. 1 to 6, but with the shroud (8) in the closed position. The shroud is able to move between the open and closed position by pivoting at pivot points (7, 7'). Typically, the device is used by the user placing their face at the aperture (2) when the shroud is open and then closing it so that is comes down over the back of their head and excludes extraneous light from entering the aperture. The shroud is lightweight and so easy to move and comfortable to rest on shoulders of the user, if required. The pivot points may comprise a clutch mechanism to allow the shroud to hold itself in any position, for example in an open position. Preferably the clutch mechanism is arranged to provide a soft closure mechanism so that the shroud may be moved between an open and a closed position but that it does not need to be held open whilst the face is placed at the aperture and so that when the face is in place it can be pulled down behind the head and does not drop down in an uncontrolled manner onto the shoulders.

The shroud is arranged to cover transparent windows placed in the housing through which a person who places his/her face at the aperture may look. This encourages the shroud to be moved to the closed position quickly in order to make the person feel more comfortable and less claustrophobic. This has the advantage of reducing the likelihood that images will be taken accidentally with the shroud open. This is advantageous because images taken with the shroud open will are likely to be of lower quality than images taken with the shroud closed because there will be higher levels of extraneous light entering the housing when the shroud is open.

Figure 9:
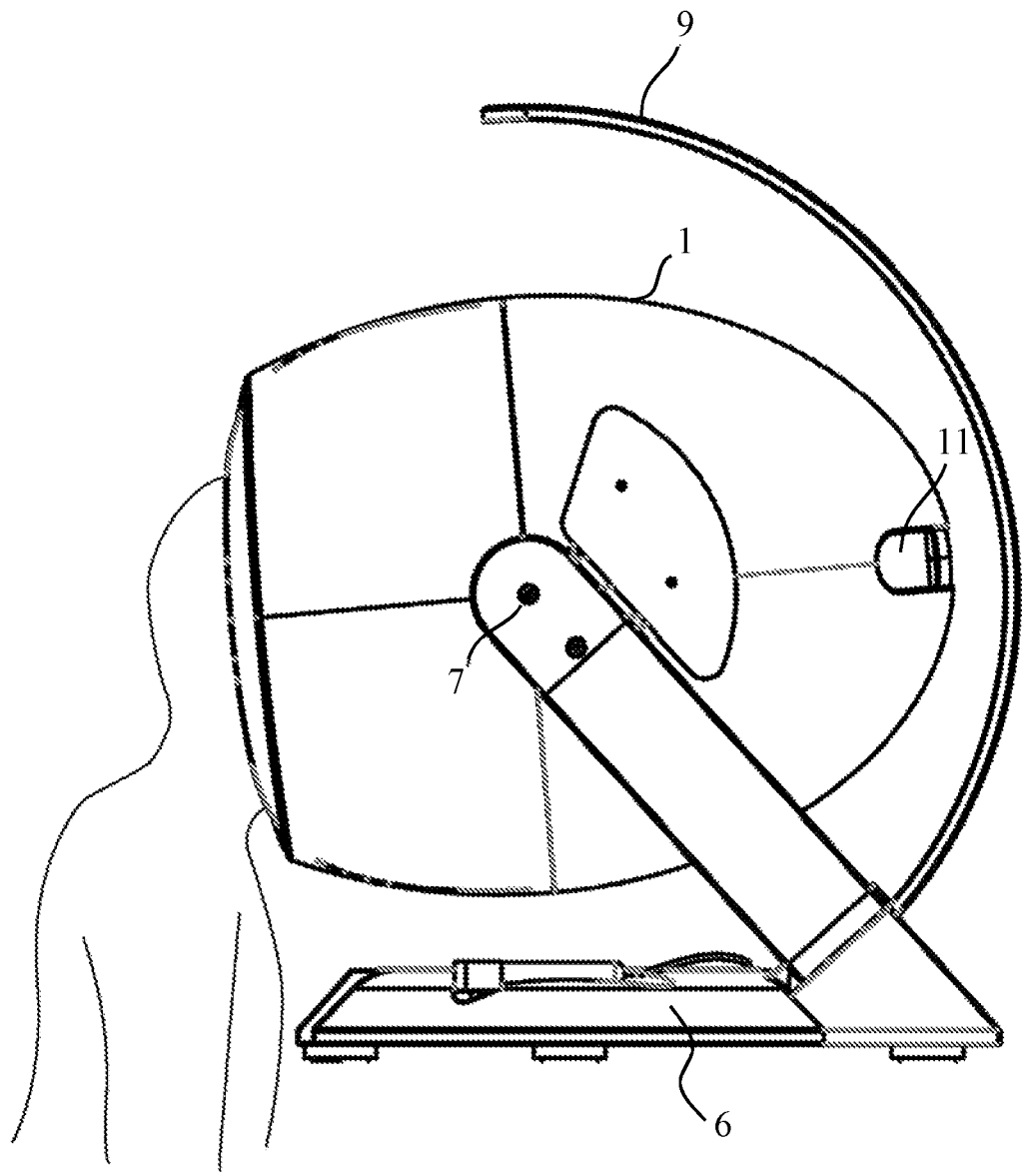
FIG. 9 shows an embodiment of a device according to the invention in use by a relatively short person.
Figure 10:
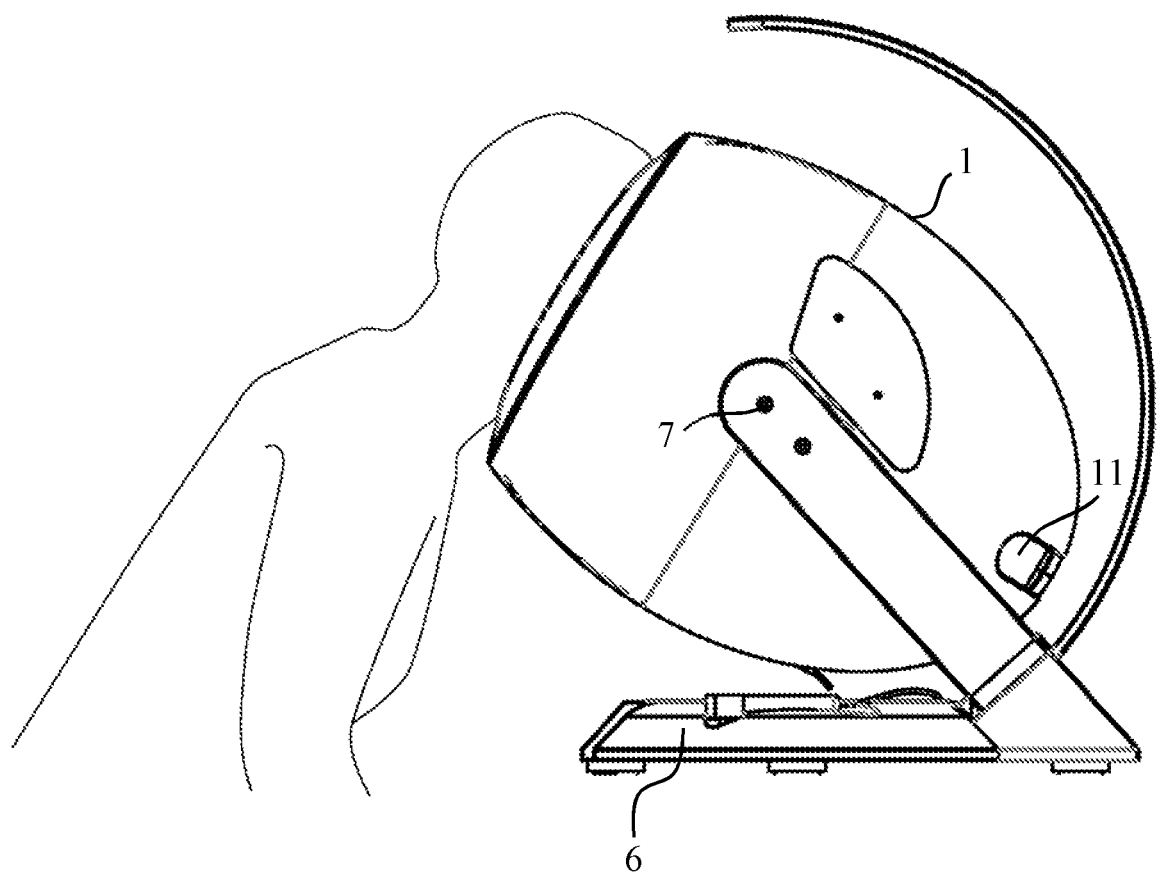
FIG. 10 shows an embodiment of a device according to the invention in use by a relatively tall person.
Figure 11:
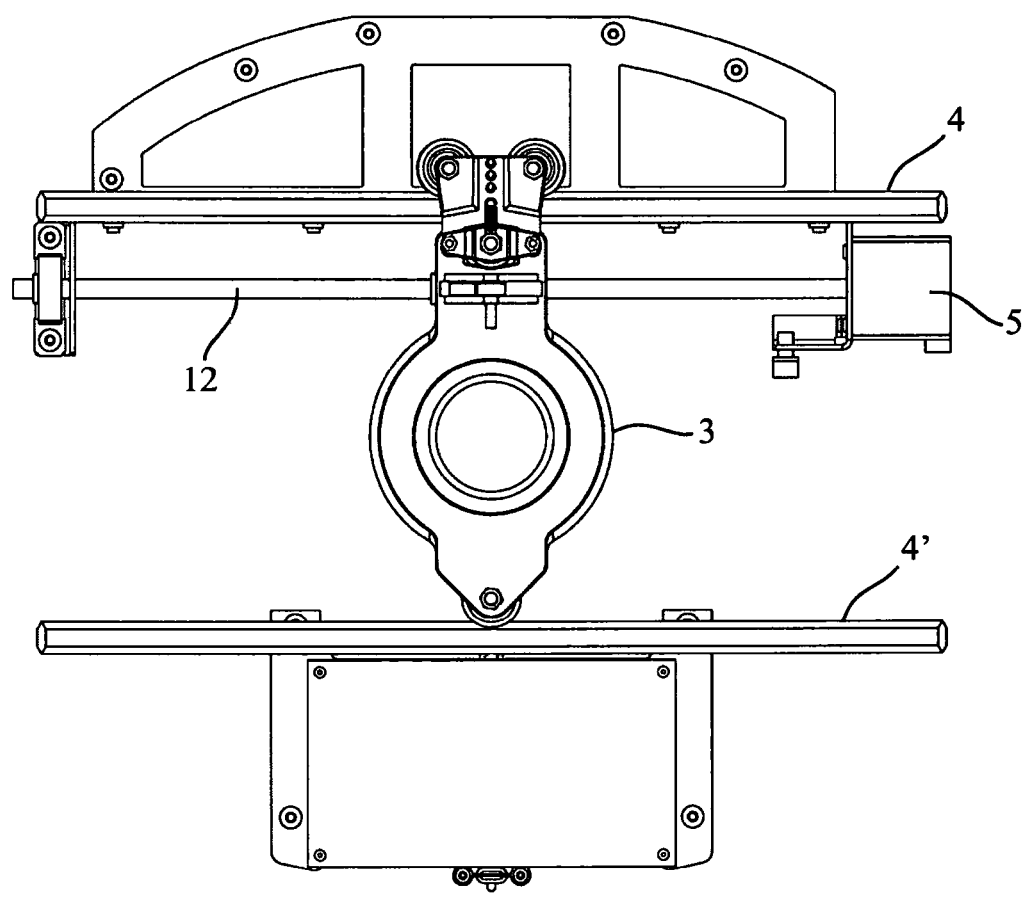
FIGS. 11 to 13 show an embodiment of a camera mounting assembly for a device in accordance with the invention.

FIGS. 9 and 10 show a device in use. For ease of illustration, the shroud is not shown in these drawings, but may be present. In use, the user places their face at the aperture as shown. They face forward and the shroud is pivoted to the closed position. The housing itself is also pivoted at the pivot points (7, 7') so that it can be tilted and the aperture consequently moved downwards or upwards to accommodate, respectively, subjects who are relatively short (as in FIG. 9), or relatively tall (as in FIG. 10). When the device is placed at tabletop height, the subject is typically seated to use the device, for example on a chair. He or she will, very naturally, lean forwards by the correct amount to place their face at the aperture and the housing will easily pivot to accommodate them. Taller people may have to push their chair back as they lean forward, but again this is a very natural movement and would not necessarily even be noticed by the user, in contrast with alternative methods of adjustment to accommodate users of different heights, which might involve adjusting the height of a chair or of the aperture by conscious use of levers, knobs or screws.

The housing (1), stand (6) and pivots (7, 7') are configured such that the tilting about the pivots occurs very easily. To achieve this, the device uses a combination of a housing which is substantially balanced about the pivot point (7, 7') and pivot points incorporating a clutch mechanism. This means that the housing may be easily moved to any tilt position and remain in that position.

Once the subject has placed their face at the aperture, the shroud can be moved to the closed position. The transparent windows (11) prevent claustrophobia and encourage the subject to look generally forward. When the subject is comfortably seated and the shroud closed, the process of taking the images can be initiated, for example by an operator using an input device such as a tablet. The capturing of the images involves the camera moving between a position perpendicular to the face where a "straight-on" image is captured and positions offset laterally from the perpendicular position to capture images of each side of the face.

The position of the camera, the extent of the lightness, the occlusion of the windows, the operation of the camera and the presentation and subsequent processing of the images captured is controlled by touchscreen tablet 13.

Figure 12:
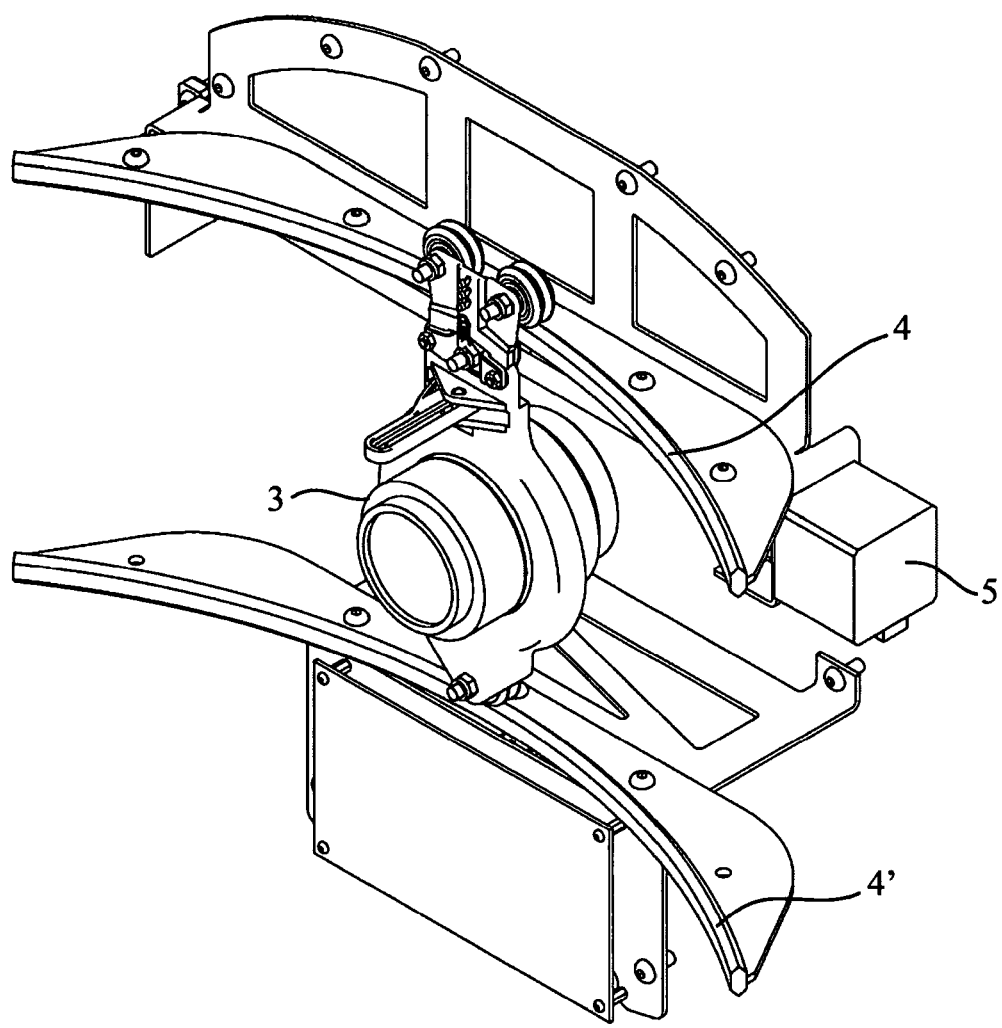
Figure 13:
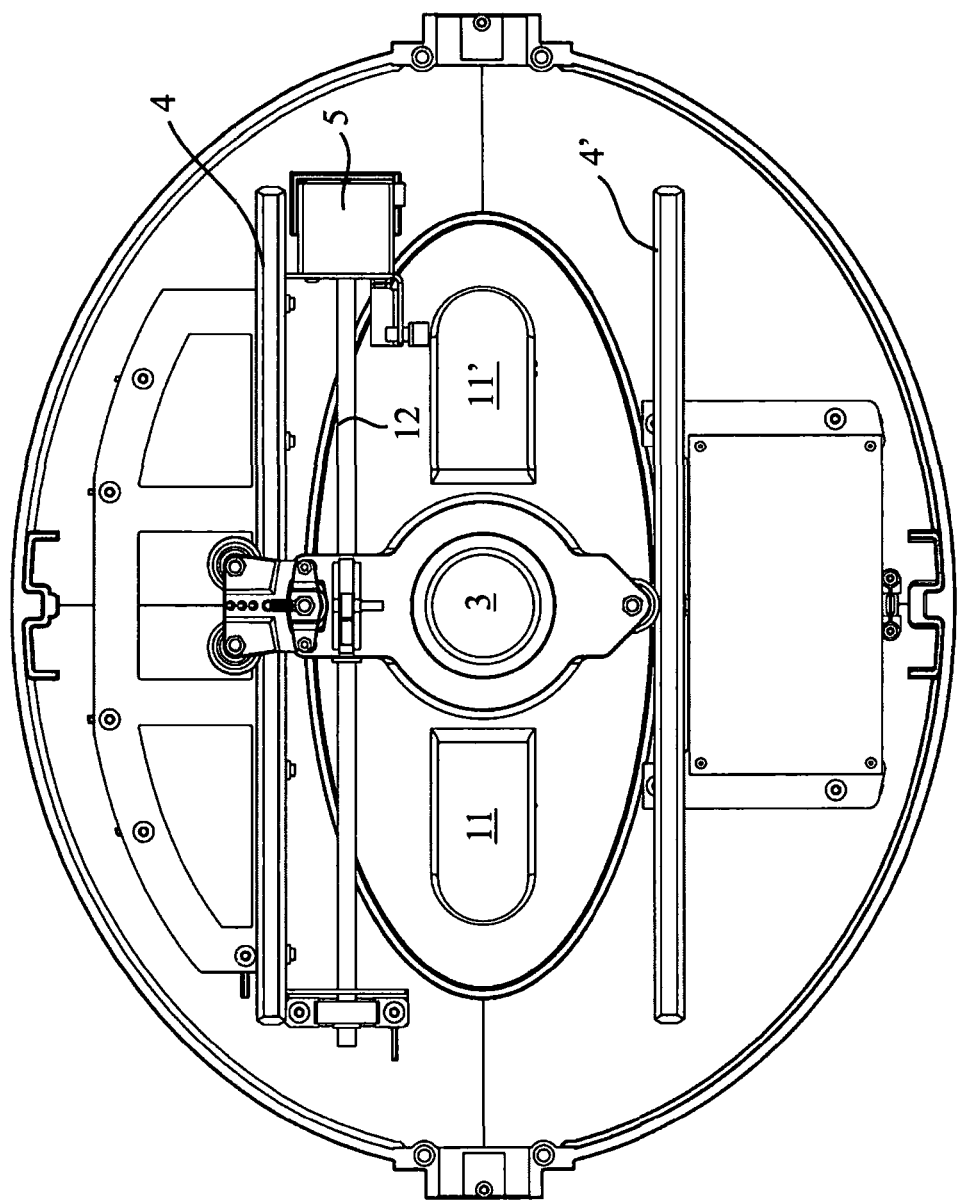

FIG. 12 shows an exemplary arrangement by which a camera can move. The camera (3) is mounted on rails, a top rail (4) and a bottom rail (4'). The rails are curves so as to maintain an approximately constant distance from the face. The camera (3) is moved along the rail by a lead screw (12), driven by a motor (5).

The housing is provided with internal lighting which is polarized by means of a suitable filter. The camera is also polarized by means of a suitable filter. The filters are cross-polarized with respect to each other in order to reduce the reflective glare from the skin surface.

Figure 16:
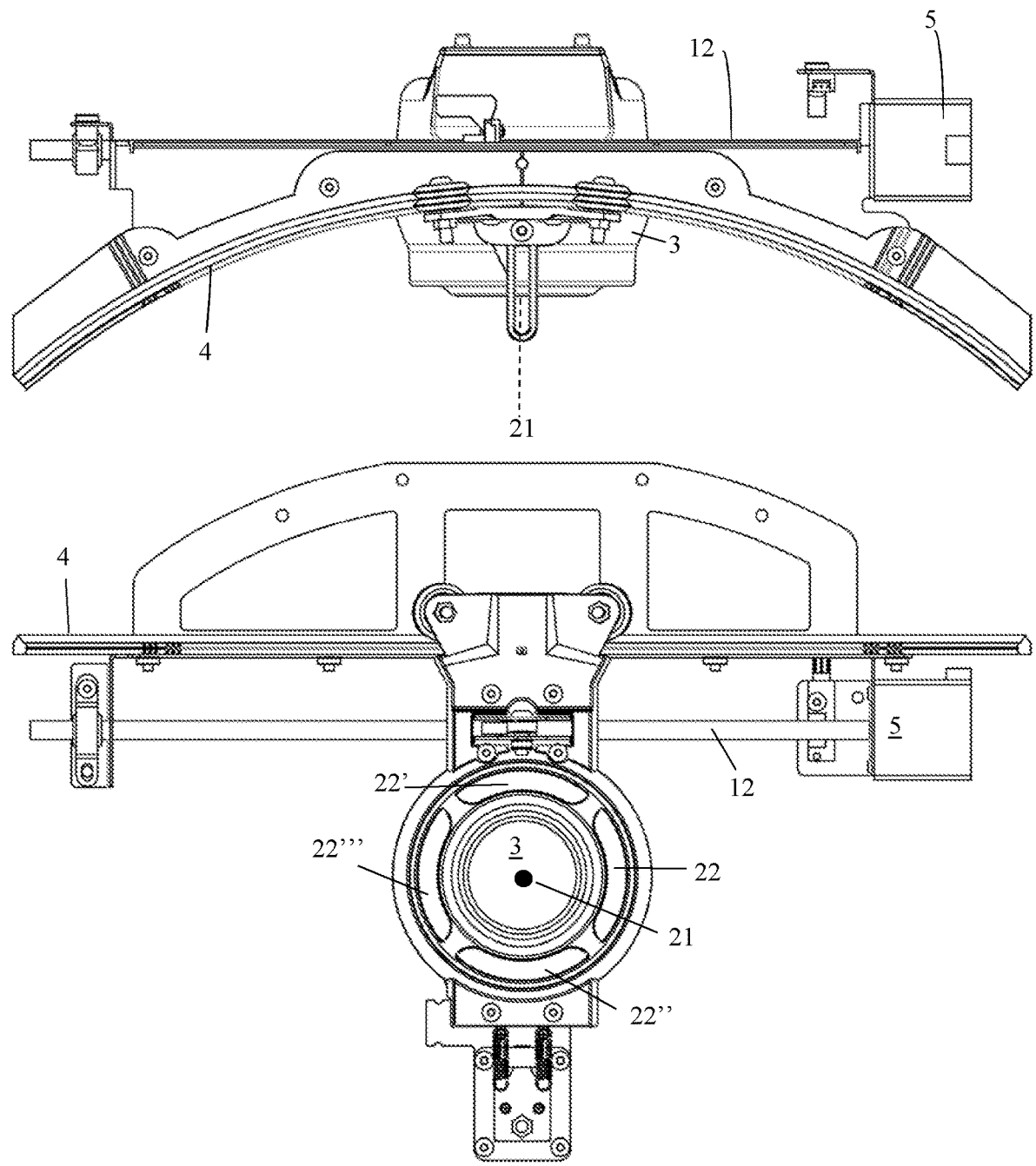
FIG. 16 shows an embodiment of the mounting assembly for the camera and light source for a device in accordance with the third aspect of the invention.
Figure 17:
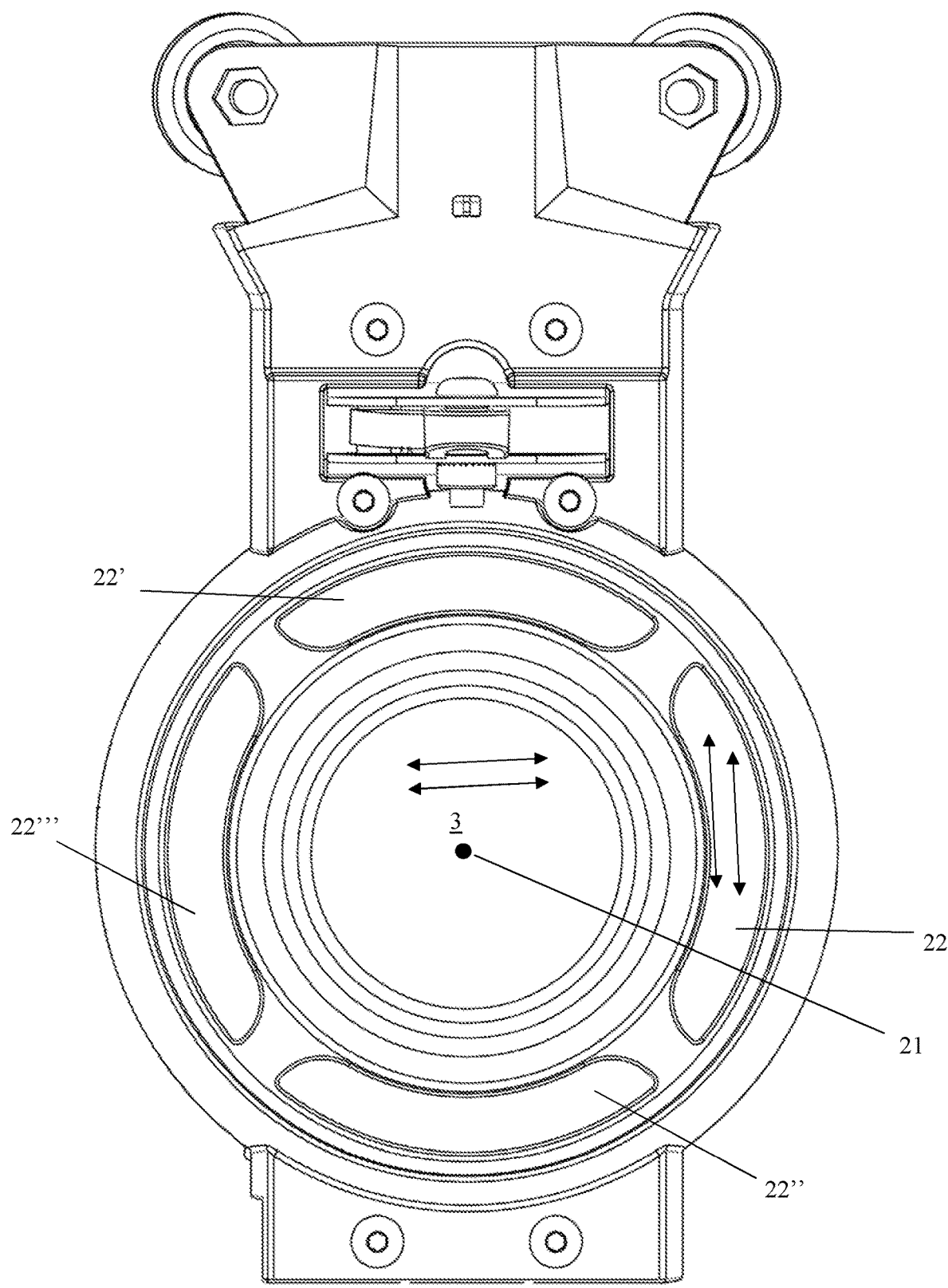
FIG. 17 shows a close up of an embodiment of the a lens and light source of a device in accordance with the third aspect of the invention

FIGS. 16 and 17 show features of a device which is an embodiment of a device of the invention. Features of a device in accordance with the third aspect of the invention are especially well illustrated in FIGS. 16 and 17, but such features may also be present in a device which accords with a device of the first aspect of the invention.

FIG. 16 shows two views of an exemplary arrangement by which a camera can move. The camera (3) is mounted on a rail (4) which can be seen to curve in an arc in the upper image. Similarly to the arrangement shown in FIG. 12, the camera (3) is driven to move along the rail by a lead screw (12), driven by a motor (5). The upper image shows the optical axis (21) of the camera lens (20). In the lower image the optical axis of the camera lens points straight out of the page from point (21). In the embodiment shown in FIG. 16 the camera (3) is mounted alongside the source of polarized light such that the camera moves together with the source if polarized light driven by the lead screw (12).

FIG. 17 is an enlargement of party of the assembly shown in FIG. 16. As can be seen the source of polarized light is 4 regions (22, 22', 22", 22'") containing LED lights behind polarizing filters which surround the lens of camera (3). Also shown in FIG. 17 is the direction of the linear polarization of the light source and the filter on the camera lens (shown diagrammatically by double-headed arrows). It can be seen that the respective directions are at 90 degrees to each other (i.e. they are cross-polarized)

Example Images

Figure 14:
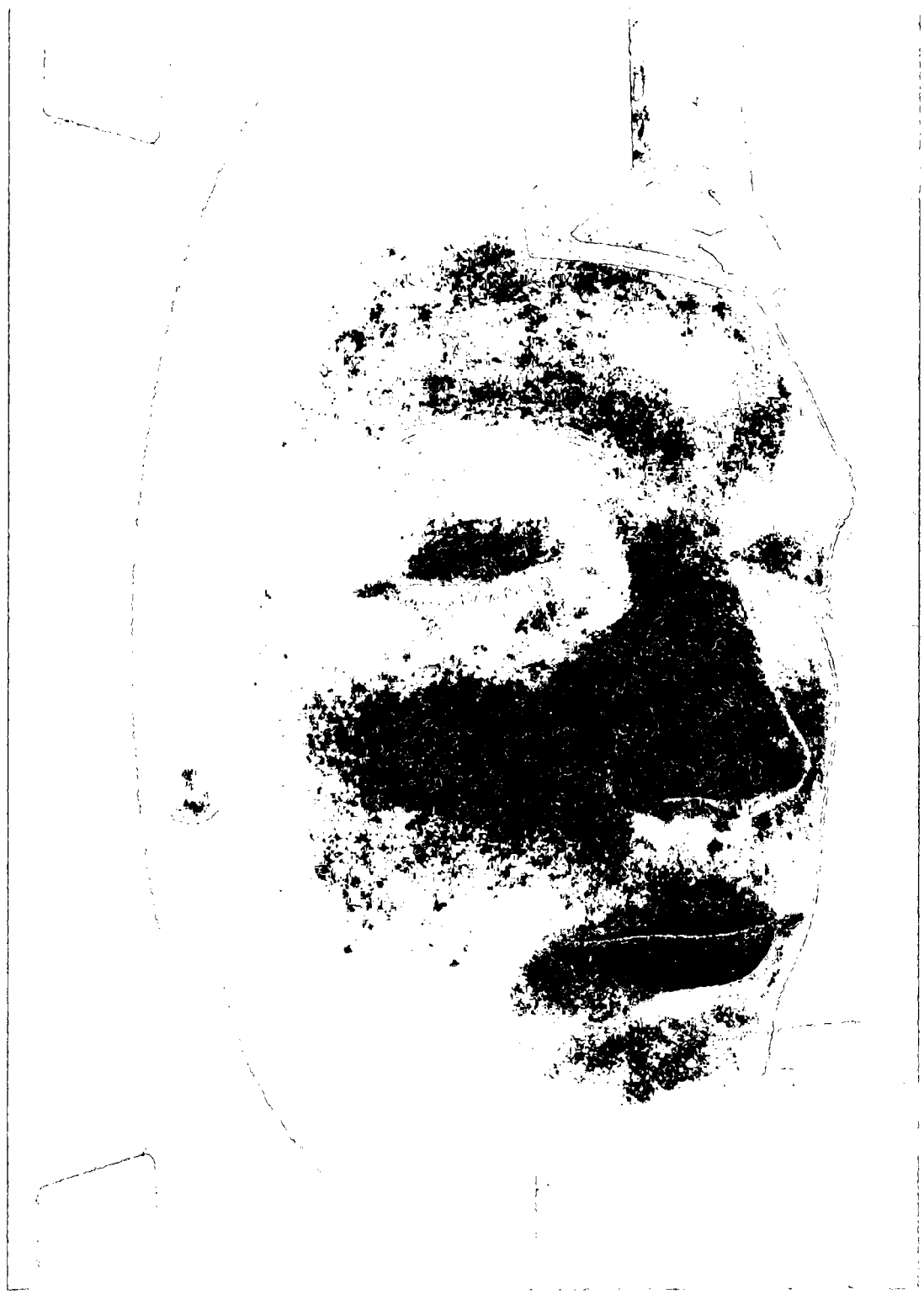
FIG. 14 shows a photograph of a human face using a device of the invention with unpolarized light.
Figure 15:
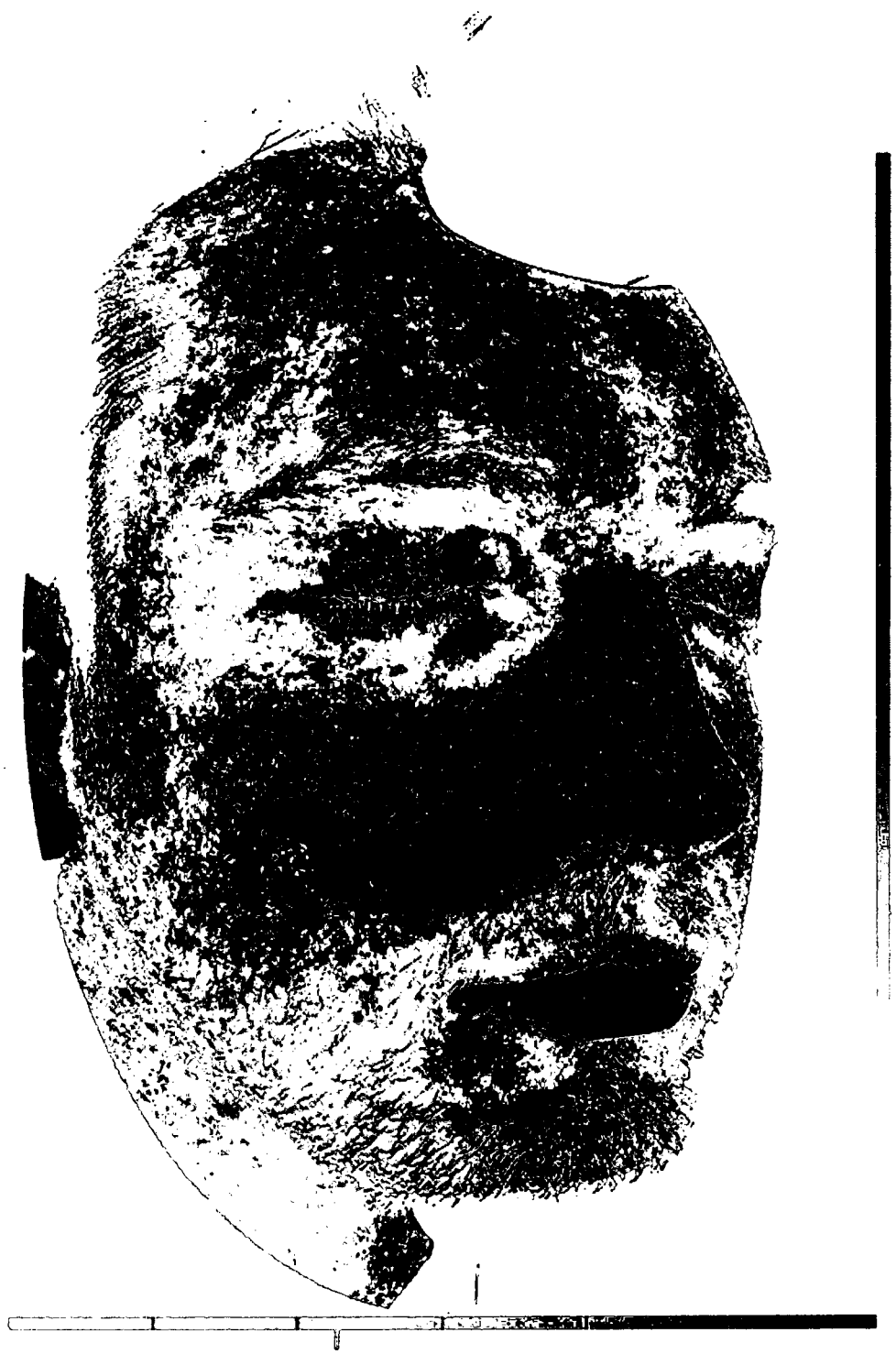
FIG. 15 shows a photograph of a human face using a device of the invention with polarized light.

In order to illustrate the advantages of using polarized light in accordance with the present invention in its third and fourth aspect or as an optional feature in accordance with the first or second aspect, two comparative photographs of the same human face were taken with the device according to the invention as described in the example above. The device was arranged with the shroud lowered to exclude almost all external light and with the windows closed during image capture. The face was illuminated with white light at 4000 k and UV light of 365 nm wavelength. The first image (FIG. 14) was produced without the use of cross polarization between the camera lens and the light source. The second image (FIG. 16) was obtained with the use of cross polarization between the camera lens and the light source. Subcutaneous Skin redness can be seen in the cross-polarized image (shown as dark marks in the black and white reproduction of the images) which was not normally visible. A comparison of the two images shows that much more redness is detectable in FIG. 15 than in FIG. 14, showing that the use of cross polarization in accordance with the invention produces a superior image. This superior result is only obtained when the polarized light is provided in a direction close to the optical axis of the camera in accordance with the invention. When the polarized light is provided from a direction too far off the optical axis of the camera the advantages of using polarization are substantially lost and the image looks more like FIG. 14 than FIG. 15.

The invention claimed is:

1. A device for photographing a human face comprising:
   a) a light-excluding housing configured to receive the human face at an aperture in a) said housing, which housing includes one or more transparent or open windows in it through which a subject having their face received at the aperture is able to look forward, wherein the windows are provided with means to become closed, covered or opaque; and
   b) a camera and a light source mounted inside the housing, wherein the mounting of the camera and the light source is configured so that the camera and light source are moveable together relative to the housing;
   wherein the camera comprises a lens having an optical axis and the light source is configured to illuminate the human face to be received at the aperture, and wherein the camera lens is provided with a linear polarization filter and the light source is configured to produce illumination which is cross polarized relative to said linear polarization filter, wherein the angle between the light source and the camera lens is less than 30 degrees wherein the angle is measured at a point 200 mm along the optical axis from the camera lens, wherein the housing includes means, internal to the housing, to illuminate the human face received at the aperture.

2. The device as claimed in of claim 1, wherein the housing is provided with one or both of a chin-rest and forehead rest configured to engage with the human face at the aperture of the housing.

3. The device as claimed in claim 1, wherein the camera in mounted in the light-excluding housing such that it is able to move between a position where the camera is in the anteroposterior plane of the human face received at the aperture and positions where the camera is in a position of at least 30° to the left or right of the anteroposterior plane of the human face.

4. The device as claimed in claim 1 wherein the light source is mounted together with the camera such the light source is moveable together with the camera relative to the housing.

5. The device as claimed in claim 1, wherein the housing is mounted on a stand at one or more rotatable pivot points such that rotation about said pivot points results in movement of the aperture upward and/or downwards.

6. The device as claimed in claim 1, comprising artificial lighting provided inside the housing and configured to illuminate the human face received at the aperture.

7. The device as claimed in claim 6, wherein a control of the brightness of the artificial lighting is configured such that the brightness is adjusted in dependence of the position of the camera.

8. The device as claimed in claim 1 further comprising a light excluding shroud moveable downwards to a position behind the head of the human face received at the aperture.

9. The device as claimed in claim 8, wherein the shroud is configured to move to the position behind the head of the human who has had their face received at the aperture by rotation which is about one or more pivot points.

10. A method of providing images of a human face placed at an aperture of a light excluding housing comprising illuminating the human face with linearly-polarized light, and capturing an image of the face with a camera having a lens with a linear polarization filter which is cross-polarized relative the illumination, wherein the angle between the light source and the camera lens is less than 30 degrees wherein the angle is measured at a point 200 mm along the optical axis from the camera lens and wherein the housing includes one or more transparent or open windows in it through which a subject having their face received at the aperture is able to look forward, wherein the windows are provided with means to become closed, covered or opaque.

11. The method according to claim 10, including the further steps of storing the captured images on a cloud server.

12. The method according to claim 10, including the further step of using a hand-held probe to measure a parameter of the skin of said human face.

* * * * *